United States Patent [19]
Winkelmann et al.

[11] 3,991,191
[45] Nov. 9, 1976

[54] ANTIPROTOZOAL
(1-ALKYL-5-NITRO-IMIDAZOLYL-2-
ALKYL)-PYRIMIDINES

[75] Inventors: Erhardt Winkelmann, Kelkheim, Taunus; Akhileswer Sinharay, Frankfurt am Main; Wolfgang Raether, Dreieichenhain, all of Germany

[73] Assignee: Hoechst Aktiengesellschaft, Frankfurt am Main, Germany

[22] Filed: Jan. 22, 1975

[21] Appl. No.: 543,165

[30] Foreign Application Priority Data
Jan. 24, 1974 Germany............................ 2403340

[52] U.S. Cl.............................. 424/251; 260/250 A; 260/250 B; 260/250 BN; 260/256.5 R; 424/250

[51] Int. Cl.²............... A61K 31/505; C07D 239/28
[58] Field of Search............... 260/256.5 R; 424/251

[56] References Cited
UNITED STATES PATENTS
3,557,115  1/1971  Manning ...................... 260/256.5 R Primary Examiner—Leonard Schenkman
Attorney, Agent, or Firm—Curtis, Morris & Safford

[57] ABSTRACT

New (1-alkyl-5-nitro-imidazolyl-2-alkyl)-heteroaryl compounds are disclosed as well as a process for their manufacture.

The new compounds are effective against pathogens, such as bacteria and protozoa, as well as against fungi.

10 Claims, No Drawings

ANTIPROTOZOAL (1-ALKYL-5-NITRO-IMIDAZOLYL-2-ALKYL)-PYRIMIDINES

The present invention relates to (1-alkyl-5-nitro-imidazolyl-2-alkyl)-heteroaryl compounds and to a process for preparing them.

It is known to use 1-(2-hydroxyethyl)-2-methyl-5-nitro-imidazole (Metronidazol) for the treatment of protozoal diseases, such as trichomoniasis and amebiasis.

The present invention relates to (1-alkyl-5-nitro-imidazolyl-2-alkyl)-heteroaryl sulfides, sulfoxides and sulfones of the formula I

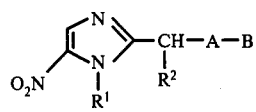
(I), in which $R^1$ stands for a methyl or ethyl group, $R^2$ for a hydrogen atom or a methyl group, A for a sulfur bridge (—S—), a sulfoxide group (—SO—) or a sulfone group (—SO$_2$—) and B for a pyridazine ring

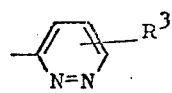

a pyrimidine ring

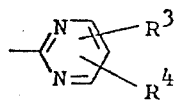 or 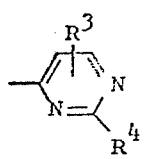

or a pyrazine ring

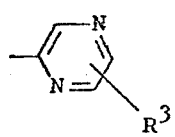

which is linked in the said manner to the sulfur bridge, the sulfoxide group or sulfone group, and in which the radicals $R^3$ and $R^4$ represent, independently from each other, a hydrogen atom, a methyl or methoxy group, a halogen atom, such as fluorine, chlorine, bromine or iodine, a cyano group or a nitro group.

The new compounds are effective against various protozoa, in particular against trichomonads and amebae, as well as against trypanosoma and bacteria.

The present invention further relates to is a process for the manufacture of (1-alkyl-5-nitro-imidazolyl-2-alkyl)-heteroaryl sulfides, sulfoxides and sulfones of the above-mentioned formula I, which comprises a. reacting 1-alkyl-2-halogen alkyl-5-nitro-imidazoles of the formula II

in which $R^1$ and $R^2$ have the meaning mentioned above in formula I, and X stands for a halogen atom or an acyloxy group, preferably acetoxy, propoxy, butoxy, benzoyloxy, benzyloxy, or tolyloxy, or an arylsulfonic acid ester group, preferably a benzene-sulfonic acid ester group, a toluene-sulfonic acid ester group or a naphthalene-sulfonic acid ester group, with a heteroaryl mercaptan or the alkali metal or ammonium salt thereof corresponding to the formula III $$Y - S - B \qquad (III),$$

in which Y stands for hydrogen, an alkali metal, especially sodium or potassium, or ammonium, and B is defined as in formula I above, or b. reacting a 1-alkyl-2-mercapto-alkyl-5-nitro-imidazole of the formula IV

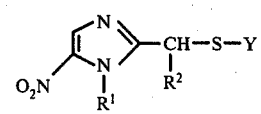

in which $R^1$, $R^2$ and Y are defined as above, with a heteroaryl halide of the formula V $$X - B \qquad (V),$$

in which X and B are defined as above, and, optionally, oxidizing the sulfide compound of formula I thus obtained to yield a sulfoxide or sulfone.

As starting compounds of formula II, there may be mentioned, for example, 1-methyl-, 1-ethyl-2-chloro-, 2-bromo-, -2- iodo-methyl- or 1-methyl-, 1-ethyl-2-chloro-, -2-bromo, -2-iodo-(1-ethyl)-5-nitro-imidazole, 1-methyl- and/or 1-ethyl-2-acetoxy-5-nitro-imidazole- or 1-methyl- and/or 1-ethyl-2-benzene- and/or -2-toluene-sulfonic acid ester.

As starting products of formula III, there are mentioned, for example, 3-mercapto-pyridazine, 2- or 4- mercapto-pyrimidine, 2-mercapto-pyrazine, 3-mercapto-6-methyl-, 3-mercapto-6-methoxypyridazine, 3-mercapto-6-cyano-pyridazine, 3-mercapto-4-, -5-fluoro-(chloro, bromo, iodo)-pyridazine, 2-mercapto-4- or -5-methyl- and/or 4- or -5-methoxy-pyrimidine, 2-mercapto-4,6-dimethyl-and/or 4,6-dimethoxy-pyrimidine, 2-mercapto-4-methyl-6-methoxy-pyrimidine, 2-mercapto-4- or -5-cyano-pyrimidine, 2-mercapto-5-nitro-pyrimidine, 2-mercapto-5-fluoro (chloro, bromo, iodo)-pyrimidine, 4-mercapto-2- or -6-methyl-and/or -2- or -6-methoxy-pyrimidine, 4-mercapto-2,6-dimethyl-, and/or -2,6-dimethoxy-pyrimidine, 4-mercapto-2-methyl-6-methoxy-pyrimidine, 4-mercapto-2-methoxy-6-methyl-pyrimidine, 4-mercapto-5-fluoro (chloro, bromo, iodo)-pyrimidine, 4-mercapto-5-nitro-pyrimidine, 4-mercapto-5- or -6-cyano-pyrimidine, 2-mercapto-3- or -5-methyl- and/or -3- or -5-methoxy-pyrazine, 2-mercapto-3- or -5-cyano-pyrazine.

Instead of the above-mentioned free mercapto compounds, the alkali metal or ammonium salts thereof, or mercaptan-yielding substances, such as isothiouronium salts, may also be used.

As starting substances of formula Iv, there are mentioned, for example, 1-methyl-, 1-ethyl-2-mercaptomethyl- or 1-methyl-, 1-ethyl-2-mercapto-(1-ethyl)-5-nitro-imidazoles or the alkali metal or ammonium salts thereof, or mercapto-yielding agents, such as isothiouronium salts.

As starting compounds of formula V, there are mentioned, for example, all the compounds as mentioned for formula III, wherein, however, the mercapto group is replaced by fluorine, chlorine, bromine, or iodine, or an acetoxy- or benzene- and/or toluene-sulfonic acid ester group.

The 1-alkyl-2-chloroalkyl-nitro-imidazoles of formula II used as starting compounds, are obtained by reacting 1-alkyl-2-hydroxyalkyl-5-nitro-imidazoles with thionyl chloride, which may be converted, optionally, into the corresponding fluorinated, brominated, or iodinated compounds by a reaction with other metal halides.

The 1-alkyl-2-acyloxy-alkyl-5-nitro-imidazoles or 1-alkyl-2-(arylsulfonyloxy-alkyl)-5-nitro-imidazoles of formula II, also used as starting compounds, are obtained by reacting 1-alkyl-2-hydroxyalkyl-5-nitro-imidazoles with an acid anhydride or acid chloride, such as acetic anhydride or acetyl chloride, or with an arylsulfonic acid chloride, such as 4-toluene-sulfonic acid chloride.

The heteroaryl mercaptans of formula III used as starting compounds are prepared by reacting corresponding halogeno-heterocyclic compounds with hydrogen sulfide.

The 1-alkyl-2-mercapto-alkyl-5-nitro-imidazoles of formula IV used as starting compounds are obtained by reacting corresponding 2-halogeno-alkyl-5-nitro-imidazoles with hydrogen sulfide.

The halogeno-heterocyclic compounds of formula V used as starting substances are prepared by reacting the corresponding hydroxy compounds with phosphorus halides.

The two variants (a) and (b) of the process of the invention are advantageously carried out using equimolar amounts of each starting substance, preferably in a solvent or dispersing agent. If the free mercapto compounds of formula III or IV are used, the solvent used is preferably a polar one; when the salts thereof are used, the solvent chosen is preferably a non polar one.

As non polar solvents, there are mentioned, for example, benzene, toluene, xylene, or chlorobenzene. As polar solvents, there are mentioned, for example, alcohols, such as methanol, ethanol, propanol, butanol, methoxy-ethanol, or ketones, such as acetone, methylethyl-ketone, methylbutyl-ketone; further pyridine, picoline, quinoline, dimethylformamide, dimethylacetamide, N-methyl-pyrrolidone, tetra-methyl-urea, hexamethyl-phosphoric acid triamide, or dimethyl-sulfoxide.

The reaction temperatures may generally be in the range of from 0° to 150° C, preferably between 20° and 80° C. In this connection, the reactions using polar solvents may be carried out at lower temperatures, those using non-polar solvents suitably at elevated temperatures. Depending on the temperatures chosen, the reaction times range from a few minutes to several hours.

If the free mercapto compounds of formulae III and IV are used, it is advisable to use an acid-binding agent. As agents of this kind, use may be made of bases, such as triethylamine or pyridine, as well as alkali metal and alkaline earth metal carbonates and bicarbonates, hydroxides and alkoxides, for example, the methoxides, ethoxides and butoxides.

The products of the invention are isolated according to the usual methods, by distilling off the solvents used or by diluting the reaction solution with water. Optionally, the products may be purified by a recrystallization from an appropriate solvent or solvent mixture.

The sulfides of formula I (A = —S—) obtained according to one of the above-mentioned process variants (a) or (b), may be converted by oxidation into the corresponding sulfoxides (A = —SO—) and/or sulfones (A = —SO$_2$—).

The oxidation reactions are advantageously carried out using simple or double molar amounts of an oxidizing agent. The treatment of the sulfides with one mol-equivalent of the oxidizing agent yields sulfoxides, with two mol-equivalents of oxidizing agent, it yields sulfones. As oxidizing agents, there may be used, for example, hydrogen peroxide or peroxo acids, such as peracetic acid, pertrifluoroacetic acid or meta-chloroperbenzoic acid, as well as nitric acid or chromic acid, and/or the salts thereof, moreover, permanganates, hypochlorites, perchlorates, periodates, and nitrogen oxides. The oxidation reactions are advantageously carried out in a solvent or dispersing agent.

For this purpose, those solvents are particularly useful which are not attacked by the oxidizing agent, for example, acetic acid or trifluoroacetic acid. When perbenzoic acid is used, methylene chloride or chloroform are also useful as solvents.

The oxidation reactions which are to yield sulfoxides are generally carried out at temperatures ranging from 10° to 30° C. The sulfones are generally obtained at oxidation temperatures of from 50° to 100° C. The sulfones may also be prepared, optionally, by oxidation of the corresponding sulfoxides, by means of the above-specified oxidizing agents at elevated temperatures.

Depending on the temperature chosen and on the desired final product, the oxidation times range from a few minutes to several hours.

The products of the invention are isolated by diluting the reaction solution with water and, at the same time, precipitating them, or by evaporating the organic solvent under reduced pressure. They may be purified, where required, by recrystallizing them from a suitable solvent or mixture of solvents.

The new compounds of formula I are well compatible and are effective against pathogens, such as bacteria and protozoa, as well as against fungi. They are especially active against trichomonads and amebae and are in this respect superior to the known Metronidazol. The individual dosage unit ranges from 5 to 100 mg/kg of body weight.

The new compounds of formula I are therefore suitable for the treatment of protozoal diseases in mammals, as they are caused, for example, by infections with Trichomonas vaginalis and Entamoeba histolytica, as well as with trypanosoma cruci, trypanosoma brucei and trypanosoma congolense.

The compounds of the invention can be administered orally or locally. The dosage unit for oral administration is given in the usual forms for pharmaceutical preparations, for example, tablets or capsules containing, per daily dosage unit, about 10 to 750 mg, preferably 150 to 500 mg, of the active substance in combination with a usual carrier substance and/or constituent. For local application, for example, jellies, creams, ointments or suppositories are useful.

The following Examples serve to illustrate the invention.

EXAMPLES

1.

1-Methyl-2-(pyrimidinyl-2-thiomethyl)-5-nitro-imidazole 2.3 Grams (0.1 mol) of metallic sodium were dissolved in small portions in 50 ml of anhydrous methanol. In this sodium methylate solution, 11.2 g. (0.1 mol) of 2-mercapto-pyrimidine as a solution in 70 ml of anhydrous methanol were introduced, and the solution was concentrated by evaporation under reduced pressure. The residue was combined with a solution of 17.55 g (0.1 mol) of 1-methyl-2-chloro-methyl-5-nitro-imidazole in 100 ml of dimethyl acetamide, and the reaction mixture was heated at 40° C for 1 hour. After cooling, water was added to the solution until crystallization set in. The end product was filtered off and recrystallized from ethanol while charcoal was added.

In this manner, 21.3 g of 1-methyl-2-(pyrimidinyl-2-thiomethyl)-5-nitro-imidazole (corresponding to 85% of the theoretical yield) were obtained in the form of yellowish crystals, m.p. 143° C.

In the same manner, the following compounds were obtained in good yields:

2. 1-methyl-2-(4-methyl-pyrimidinyl-2-thiomethyl)-5-nitro-imidazole, melting point 138° C, from 1-methyl-2-chloromethyl-5-nitro-imidazole and 4-methyl-2-mercapto-pyrimidine;

3. 1-methyl-2-(5-methyl-pyrimidinyl-2-thiomethyl)-5-nitro-imidazole, melting point 122° C, from 1-methyl-2-chloromethyl-5-nitro-imidazole and 5-methyl-2-mercapto-pyrimidine;

4. 1-methyl-2-(4,6-dimethyl-pyrimidinyl-2-thiomethyl)-5-nitro-imidazole, m.p. 111° C, from 1-methyl-2-chloromethyl-5-nitro-imidazole and 4,6-dimethyl-2-mercapto-pyrimidine;

5. 1-methyl-2-(4-methoxy-pyrimidinyl-2-thiomethyl)-5-nitro-imidazole, m.p. 196° C, from 1-methyl-2-chloromethyl-5-nitro-imidazole and 4-methoxy-2-mercapto-pyrimidine;

6. 1-methyl-2-(4-methyl-6-methoxy-pyrimidinyl-2-thiomethyl)-5-nitro-imidazole, m.p. 165° C, from 1-methyl-2-chloromethyl-5-nitro-imidazole and 4,6-dimethoxy-2-mercapto-pyrimidine;

7. 1-methyl-2-(5-chloro-pyrimidinyl-2-thiomethyl)-5-nitro-imidazole, m.p. 127° C, from 1-methyl-2-chloromethyl-5-nitro-imidazole and 5-chloro-2-mercapto-pyrimidine;

8. 1-methyl-2-(5-cyano-pyrimidinyl-2-thiomethyl)-5-nitro-imidazole, m.p. 158° C, from 1-methyl-2-chloromethyl-5-nitro-imidazole and 5-cyano-2-mercapto-pyrimidine;

9. 1-methyl-2-(5-nitro-pyrimidinyl-2-thiomethyl)-5-nitro-imidazole, m.p. 127° C, from 1-methyl-2-chloromethyl-5-nitro-imidazole and 5-nitro-2-mercapto-pyrimidine;

10. 1-ethyl-2-(pyrimidinyl-2-thiomethyl)-5-nitro-imidazole, m.p. 64° C, from 1-ethyl-2-chloromethyl-5-nitro-imidazole and 2-mercapto-pyrimidine;

11. 1-methyl-2-[pyrimidinyl-2-thio(1-ethyl)]-5-nitro-imidazole, m.p. 58° C, from 1-methyl-2-chloro-(1-ethyl-5-nitro-imidazole and 2-mercapto-pyrimidine;

12. 1-methyl-2-(pyridazinyl-3-thiomethyl)-5-nitro-imidazole, m.p. 172° C, from 1-methyl-2-chloromethyl-5-nitro-imidazole and 3-mercapto-pyridazine;

13. 1-methyl-2-(6-methyl-pyridazinyl-3-thiomethyl)-5-nitro-imidazole, m.p. 162° C, from 1-methyl-2-chloromethyl-5-nitro-imidazole and 6-methyl-3-mercapto-pyridazine;

14. 1-methyl-2-(6-methoxy-pyridazinyl-3-thiomethyl)-5-nitro-imidazole, m.p. 92° C, from 1-methyl-2-chloromethyl-5-nitro-imidazole and 6-methoxy-3-mercapto-pyridazine;

15. 1-methyl-2-(pyrimidinyl-4-thiomethyl)-5-nitro-imidazole, m.p. 111° C, from 1-methyl-2-chloromethyl-5-nitro-imidazole and 4-mercapto-pyrimidine;

16. 1-methyl-2-(2,6-dimethyl-pyrimidinyl-4-thiomethyl)-5-nitro-imidazole, m.p. 100° C, from 1-methyl-2-chloromethyl-5-nitro-imidazole and 2,6-dimethyl-4-mercapto-pyrimidine;

17. 1-methyl-2-(2,6-dimethoxy-pyrimidinyl-4-thiomethyl)-5-nitro-imidazole, m.p. 145° C, from 1-methyl-2-chloromethyl-5-nitro-imidazole and 2,6-dimethoxy-4-mercapto-pyrimidine;

18. 1-methyl-2-(pyrazinyl-2-thiomethyl)-5-nitro-imidazole, m.p. 146° C, from 1-methyl-2-chloromethyl-5-nitro-imidazole and 2-mercapto-pyrazine.

In an analogous manner, the following compounds were obtained from the corresponding starting products:

19. 1-methyl-2-(5-methoxy-pyrimidinyl-2-thiomethyl)-5-nitro-imidazole from 1-methyl-2-chloromethyl-5-nitro-imidazole (MCNI) and 5-methoxy-2-mercapto-pyrimidine (—PI);

20. 1-methyl-2-(4,6-dimethoxy-pyrimidinyl-2-thiomethyl)-5-nitro-imidazole from MCNI and 4,6-dimethoxy-2-mercapto-PI;

21. 1-methyl-2-(2-methyl-pyrimidinyl-4-thiomethyl)-5-nitro-imidazole from MCNI and 2-methyl-4-mercapto-PI;

22. 1-methyl-2-(6-methyl-pyrimidinyl-4-thiomethyl)-5-nitro-imidazole from MCNI and 6-methyl-4-mercapto-PI;

23. 1-methyl-2-(2-methoxy-pyrimidinyl-4-thiomethyl)-5-nitro-imidazole from MCNI and 2-methoxy-4-mercapto-PI;

24. 1-methyl-2-(6-methoxy-pyrimidinyl-4-thiomethyl)-5-nitro-imidazole from MCNI and 6-methoxy-4-mercapto-PI;

25. 1-methyl-2-(2-methyl-6-methoxy-pyrimidinyl-4-thiomethyl)-5-nitro-imidazole from MCNI and 2-methyl-6-methoxy-4-mercapto-PI;

26. 1-methyl-2-(2-methoxy-6-methyl-pyrimidinyl-4-thiomethyl)-5-nitro-imidazole from MCNI and 2-methoxy-6-methyl-4-mercapto-PI;

27. 1-methyl-2-(3-methyl-pyrazinyl-2-thiomethyl)-5-nitro-imidazole from MCNI and 3-methyl-2-mercapto-pyrazine (-PA);

28. 1-methyl-2-(5-methyl-pyrazinyl-2-thiomethyl)-5-nitro-imidazole from MCNI and 5-methyl-2-mercapto-PA;

29. 1-methyl-2-(3-methoxy-pyrazinyl-2-thiomethyl)-5-nitro-imidazole from MCNI and 3-methoxy-2-mercapto-PA;

30. 1-methyl-2-(5-methoxy-pyrazinyl-2-thiomethyl)-5-nitro-imidazole from MCNI and 5-methoxy-2-mercapto-PA;

31. 1-methyl-2-(6-cyano-pyridazinyl-3-thiomethyl)-5-nitro-imidazole from MCNI and 6-cyano-3-mercapto-pyridazine (—PD);

32. 1-methyl-2-(4-cyano-pyrimidinyl-2-thiomethyl)-5-nitro-imidazole from MCNI and 4-cyano-2-mercapto-PI;

33. 1-methyl-2-(5-fluoro-pyrimidinyl-2-thiomethyl)-5-nitro-imidazole from MCNI and 5-fluoro-2-mercapto-PI;

34. 1-methyl-2-(5-bromo-pyrimidinyl-2-thiomethyl)-5-nitro-imidazole from MCNI and 5-bromo-2-mercapto-PI;

35. 1-methyl-2-(5-cyano-pyrimidinyl-4-thiomethyl)-5-nitro-imidazole from MCNI and 5-cyano-4-mercapto-PI;

36. 1-methyl-2-(6-cyano-pyrimidinyl-4-thiomethyl)-5-nitro-imidazole from MCNI and 6-cyano-4-mercapto-PI;

37. 1-methyl-2-(5-fluoro-pyrimidinyl-4-thiomethyl)-5-nitro-imidazole from MCNI and 5-fluoro-4-mercapto-PI;

38. 1-methyl-2-(5-chloro-pyrimidinyl-4-thiomethyl)-5-nitro-imidazole from MCNI and 5-chloro-4-mercapto-PI;

39. 1-methyl-2-(5-bromo-pyrimidinyl-4-thiomethyl)-5-nitro-imidazole from MCNI and 5-bromo-4-mercapto-PI;

40. 1-methyl-2-(5-nitro-pyrimidinyl-4-thiomethyl)-5-nitro-imidazole from MCNI and 5-nitro-4-mercapto-PI;

41. 1-methyl-2-(3-cyano-pyrazinyl-2-thiomethyl)-5-nitro-imidazole from MCNI and 3-cyano-2-mercapto-PA;

42. 1-methyl-2-(5-cyano-pyrazinyl-2-thiomethyl)-5-nitro-imidazole from MCNI and 5-cyano-2-mercapto-PA;

43. 1-ethyl-2-(6-methyl-pyridazinyl-3-thiomethyl)-5-nitro-imidazole from 1-ethyl-2-chloromethyl-5-nitro-imidazole (ACNI) and 6-methyl-3-mercapto-PD;

44. 1-ethyl-2-(6-methoxy-pyridazinyl-3-thiomethyl)-5-nitro-imidazole from ACNI and 6-methoxy-3-mercapto-PD;

45. 1-ethyl-2-(4-methyl-pyrimidinyl-2-thiomethyl)-5-nitro-imidazole from ACNI and 4-methyl-2-mercapto-PI;

46. 1-ethyl-2-(5-methyl-pyrimidinyl-2-thiomethyl)-5-nitro-imidazole from ACNI and 5-methyl-2-mercapto-PI.

47. 1-ethyl-2-(4-methoxy-pyrimidinyl-2-thiomethyl)-5-nitro-imidazole from ACNI and 4-methoxy-2-mercapto-PI;

48. 1ethyl-2-(5-methoxy-pyrimidinyl-2-thiomethyl)-5-nitro-imidazole from ACNI and 5-methoxy-2-mercapto-PI;

49. 1-ethyl-2-(4,6-dimethyl-pyrimidinyl-2-thiomethyl)-5-nitro-imidazole from ACNI and 4,6-dimethyl-2-mercapto-PI;

50. 1-ethyl-2-(4,6-dimethoxy-pyrimidinyl-2-thiomethyl)-5-nitro-imidazole from ACNI and 4,6-dimethoxy-2-mercapto-PI;

51. 1-ethyl-2-(4-methyl-6-methoxy-pyrimidinyl-2-thiomethyl)-5-nitro-imidazole from ACNI and 4-methyl-6-methoxy-2-mercapto-PI;

52. 1-ethyl-2-(2-methyl-pyrimidinyl-4-thiomethyl)-5-nitro-imidazole from ACNI and 2-methyl-4-mercapto-PI;

53. 1-ethyl-2-(6-methyl-pyrimidinyl-4-thiomethyl)-5-nitro-imidazole from ACNI and 6-methyl-4-mercapto-PI;

54. 1-ethyl-2-(2-methoxy-pyrimidinyl-4-thiomethyl)-5-nitro-imidazole from ACNI and 2-methoxy-4-mercapto-PI;

55. 1-ethyl-2-(6-methoxy-pyrimidinyl-4-thiomethyl)-5-nitro-imidazole from ACNI and 6-methoxy-4-mercapto-PI;

56. 1-ethyl-2-(2,6-dimethyl-pyrimidinyl-4-thiomethyl)-5-nitro-imidazole from ACNI and 2,6-dimethyl-4-mercapto-PI;

57. 1-ethyl-2-(2,6-dimethoxy-pyrimidinyl-4-thiomethyl)-5-nitro-imidazole from ACNI and 2,6-dimethoxy-4-mercapto-PI;

58. 1-ethyl-2-(2-methyl-6-methoxy-pyrimidinyl-4-thiomethyl)-5-nitro-imidazole from ACNI and 2-methyl-6-methoxy-4-mercapto-PI;

59. 1-ethyl-2-(2-methoxy-6-methyl-pyrimidinyl-4-thiomethyl)-5-nitro-imidazole from ACNI and 2-methoxy-6-methyl-4-mercapto-PI;

60. 1-ethyl-2-(3-methyl-pyrazinyl-2-thiomethyl)-5-nitro-imidazole from ACNI and 3-methyl-2-mercapto-PA;

61. 1-ethyl-2-(5-methyl-pyrazinyl-2-thiomethyl)-5-nitro-imidazole from ACNI and 5-methyl-2-mercapto-PA;

62. 1-ethyl-2-(3-methoxy-pyrazinyl-2-thiomethyl)-5-nitro-imidazole from ACNI and 3-methoxy-2-mercapto-PA;

63. 1-ethyl-2-(5-methoxy-pyrazinyl-2-thiomethyl)-5-nitro-imidazole from ACNI and 5-methoxy-2-mercapto-PA;

64. 1-ethyl-2-(pyridazinyl-3-thiomethyl)-5-nitro-imidazole from ACNI and 3-mercapto-PA;

65. 1-ethyl-2-(6-cyano-pyridazinyl-3-thiomethyl)-5-nitro-imidazole from ACNI and 6-cyano-3-mercapto-PA;

66. 1-ethyl-2-(4-cyano-pyrimidinyl-2-thiomethyl)-5-nitro-imidazole from ACNI and 4-cyano-2-mercapto-PI;

67. 1-ethyl-2-(5-cyano-pyrimidinyl-2-thiomethyl)-5-nitro-imidazole from ACNI and 5-cyano-2-mercapto-PI;

68. 1-ethyl-2-(5-nitro-pyrimidinyl-2-thiomethyl)-5-nitro-imidazole from ACNI and 5-nitro-2-mercapto-PI;

69. 1-ethyl-2-(pyrimidinyl-4-thiomethyl)-5-nitro-imidazole from ACNI and 4-mercapto PI;

70. 1-ethyl-2-(5-cyano-pyrimidinyl-4-thiomethyl)-5-nitro-imidazole from ACNI and 5-cyano-4-mercapto-PI;

71. 1-ethyl-2-(6-cyano-pyrimidinyl-4-thiomethyl)-5-nitro-imidazole from ACNI and 6-cyano-4-mercapto-PI;

72. 1-ethyl-2-(5-nitro-pyrimidinyl-4-thiomethyl)-5-nitro-imidazole from ACNI and 5-nitro-4-mercapto-PI;

73. 1-ethyl-2-(pyrazinyl-2-thiomethyl)-5-nitro-imidazole from ACNI and 2-mercapto-PA;

74. 1-ethyl-2-(3-cyano-pyrazinyl-2-thiomethyl)-5-nitro-imidazole from ACNI and 3-cyano-2-mercapto-PA;

75. 1-ethyl-2-(5-cyano-pyrazinyl-2thiomethyl)-5-nitro-imidazole from ACNI and 5-cyano-2-mercapto-PA;

76. 1-methyl-2-[6-methyl-pyridazinyl-3-thio-(1-ethyl)]-5-nitro-imidazole from 1-methyl-2-chloro-(1-ethyl)-5-nitro-imidazole (MCANI) and 6-methyl-3-mercapto-PD;

77. 1-methyl-2-[6-methoxy-pyridazinyl-3-thio-(1-ethyl)]-5-nitro-imidazole from MCANI and 6-methoxy-3-mercapto-PD;

78. 1-methyl-2-[4-methyl-pyrimidinyl-2-thio-(1-ethyl)]-5-nitro-imidazole from MCANI and 4-methyl-2-mercapto-PI;

79. 1-methyl-2-[5-methyl-pyrimidinyl-2-thio-(1-ethyl)]-5-nitro-imidazole from MCANI and 5-methyl-2-mercapto-PI;

80. 1-methyl-2-[-4-methoxy-pyrimidinyl-2-thio-(1-ethyl)]-5-nitro-imidazole from MCANI and 4-methoxy-2-mercapto-PI;

81. 1-methyl-2-[5-methoxy-pyrimidinyl-2-thio-(1-ethyl)]-5-nitro-imidazole from MCANI and 5-methoxy-2-mercapto-PI;

82. 1-methyl-2-[4,6-dimethyl-pyrimidinyl-2-thio-(1-ethyl)]-5-nitro-imidazole from MCANI and 4,6-dimethyl-2-mercapto-PI;

83. 1-methyl-2-[4,6-dimethoxy-pyrimidinyl-2-thio-(1-ethyl)]-5-nitro-imidazole from MCANI and 4,6-dimethoxy-2-mercapto-PI;

84. 1-methyl-2-[4-methyl-6-methoxy-pyrimidinyl-2-thio-(1-ethyl)]-5-nitro-imidazole from MCANI and 4-methyl-6-methoxy-2-mercapto-PI;

85. 1-methyl-2-[2-methyl-pyrimidinyl-4-thio-(1-ethyl)]-5-nitro-imidazole from MCANI and 2-methyl-4-mercapto-PI;

86. 1-methyl-2-[6-methyl-pyrimidinyl-4-thio-(1-ethyl)]-5-nitro-imidazole from MCANI and 6-methyl-4-mercapto-PI;

87. 1-methyl-2-[2-methoxy-pyrimidinyl-4-thio-(1-ethyl)]-5-nitro-imidazole from MCANI and 2-methoxy-4-mercapto-PI;

88. 1-methyl-2-[6-methoxy-pyrimidinyl-4-thio-(1-ethyl)]-5-nitro-imidazole from MCANI and 6-methoxy-4-mercapto-PI;

89. 1-methyl-2-[2,6-dimethyl-pyrimidinyl-4-thio-(1-ethyl)]-5-nitro-imidazole from MCANI and 2,6-dimethyl-4-mercapto-PI;

90. 1-methyl-2-[2,6-dimethoxy-pyrimidinyl-4-thio(1-ethyl)-]-5-nitro-imidazole from MCANI and 2,6-dimethoxy-4-mercapto-PI;

91. 1-methyl-2-[2-methyl-6-methoxy-pyrimidinyl-4-thio-(1-ethyl)]-5-nitro-imidazole from MCANI and 2-methyl-6-methoxy-4-mercapto-PI;

92. 1-methyl-2-[2-methoxy-6-methyl-pyrimidinyl-4-thio-(1-ethyl)]-5-nitro-imidazole from MCANI and 2-methoxy-6-methyl-4-mercapto-PI;

93. 1-methyl-2-[3-methyl-pyrazinyl-2-thio-(1-ethyl)]-5-nitro-imidazole from MCANI and 3-methyl-2-mercapto-PA;

94. 1-methyl-2-[5-methyl-pyrazinyl-2-thio-(1-ethyl)]-5-nitro-imidazole from MCANI and 5-methyl-2-mercapto-PA;

95. 1-methyl-2-[3-methoxy-pyrazinyl-2-thio-(1-ethyl)]-5-nitro-imidazole from MCANI and 3-methoxy-2-mercapto-PA;

96. 1-methyl-2-[5-methoxy-pyrazinyl-2-thio-(1-ethyl)]-5-nitro-imidazole from MCANI and 5-methoxy-2-mercapto-PA;

97. 1-methyl-2-[pyridazinyl-3-thio-(1-ethyl)]-5-nitro-imidazole from MCANI and 3-mercapto-PD;

98. 1-methyl-2-[6-cyano-pyridazinyl-3-thio-(1-ethyl)]-5-nitro-imidazole from MCANI and 6-cyano-3-mercapto-PD;

99. 1-methyl-2-[4-cyano-pyrimidinyl-2-thio-(1-ethyl)]-5-nitro-imidazole from MCANI and 4-cyano-2-mercapto-PI;

100. 1-methyl-2-[5-cyano-pyrimidinyl-2-thio-(1-ethyl)]-5-nitro-imidazole from MCANI and 5-cyano-2-mercapto-PI;

101. 1-methyl-2-[5-nitro-pyrimidinyl-2-thio-(1-ethyl)]-5-nitro-imidazole from MCANI and 5-nitro-2-mercapto-PI;

102. 1-methyl-2-[pyrimidinyl-4-thio-(1-ethyl)]-5-nitro-imidazole from MCANI and 4-mercapto-PI;

103. 1-methyl-2-[5-cyano-pyrimidinyl-4-thio-(1-ethyl)]-5-nitro-imidazole from MCANI and 5-cyano-4-mercapto-PI;

104. 1-methyl-2-[6-cyano-pyrimidinyl-4-thio-(1-ethyl)]-5-nitro-imidazole from MCANI and 6-cyano-4-mercapto-PI;

105. 1-methyl-2-[5-nitro-pyrimidinyl-4-thio-(1-ethyl)]-5-nitro-imidazole from MCANI and 5-nitro-4-mercapto-PI;

106. 1-methyl-2-[pyrazinyl-2-thio-(1-ethyl)]-5-nitro-imidazole from MCANI and 2-mercapto-PA;

107. 1-methyl-2-[3-cyano-pyrazinyl-2-thio-(1-ethyl)]-5-nitro-imidazole from MCANI and 3-cyano-2-mercapto-PA;

108. 1-methyl-2-[5-cyano-pyrazinyl-2-thio-(1-ethyl)]-5-nitro-imidazole from MCANI and 5-cyano-2-mercapto-PA.

109. 1-Methyl-2-(pyrimidinyl-2-sulfinyl-methyl)-5-nitro-imidazole 25.1 Grams (0.1 mol) of 1-methyl-2-(pyrimidinyl-2-thiomethyl)-5-nitro-imidazole were dissolved in 200 ml of chloroform, and 17.25 g (0.1 mol) of m-chloroperbenzoic acid dissolved in 50 ml of chloroform were added dropwise, while stirring, at room temperature. The reaction solution was then stirred for another hour at room temperature and was shaken out with dilute sodium carbonate solution. The chloroform phase was separated, the remaining solution was dried over sodium sulfate and evaporated. The residue was recrystallized from alcohol.

Thus, 18.2 g of 1-methyl-2-(pyrimidinyl-2-sulfinyl-methyl)-5-nitro-imidazole (corresponding to 68% of the theoretical yield) were obtained in the form of yellowish crystals, melting point 158° C.

In the same manner, the following compounds were obtained in good yields by oxidation of the corresponding thio compounds:

110. 1-methyl-2-(pyridazinyl-3-sulfinyl-methyl)-5-nitro-imidazole;

111. 1-methyl-2-(5-fluoro-pyrimidinyl-2-sulfinyl-methyl)-5-nitro-imidazole;
112. 1-methyl-2-(5-chloro-pyrimidinyl-2-sulfinyl-methyl)-5-nitro-imidazole;
113. 1-methyl-2-(5-bromo-pyrimidinyl-2-sulfinyl-methyl)-5-nitro-imidazole;
114. 1-methyl-2-(pyrimidinyl-4-sulfinyl-methyl)-5-nitro-imidazole;
115. 1-methyl-2-(5-fluoro-pyrimidinyl-4-sulfinyl-methyl)-5-nitro-imidazole;
116. 1-methyl-2-(5-chloro-pyrimidinyl-4-sulfinyl-methyl)-5-nitro-imidazole;
117. 1-methyl-2-(5-bromo-pyrimidinyl-4-sulfinyl-methyl)-5-nitro-imidazole;
118. 1-methyl-2-(pyrimidinyl-5-sulfinyl-methyl)-5-nitro-imidazole;
119. 1-methyl-2-(pyrazinyl-2-sulfinyl-methyl)-5-nitro-imidazole;
120. 1-methyl-2-(6-methyl-pyridazinyl-3-sulfinyl-methyl)-5-nitro-imidazole;
121. 1-methyl-2-(6-methoxy-pyridazinyl-3-sulfinyl-methyl)-5-nitro-imidazole;
122. 1-methyl-2-(4-methyl-pyrimidinyl-2-sulfinyl-methyl)-5-nitro-imidazole;
123. 1-methyl-2-(5-methyl-pyrimidinyl-2-sulfinyl-methyl)-5-nitro-imidazole;
124. 1-methyl-2-(4-methoxy-pyrimidinyl-2-sulfinyl-methyl)-5-nitro-imidazole;
125. 1-methyl-2-(5-methoxy-pyrimidinyl-2-sulfinyl-methyl)-5-nitro-imidazole;
126. 1-methyl-2-(4,6-dimethyl-pyrimidinyl-2-sulfinyl-methyl)-5-nitro-imidazole;
127. 1-methyl-2-(4,6-dimethoxy-pyrimidinyl-2-sulfinyl-methyl)-5-nitro-imidazole;
128. 1-methyl-2-(4-methyl-6-methoxy-pyrimidinyl-2-sulfinyl-methyl)-5-nitro-imidazole;
129. 1-methyl-2-(2-methyl-pyrimidinyl-4-sulfinyl-methyl)-5-nitro-imidazole;
130. 1-methyl-2-(6-methyl-pyrimidinyl-4-sulfinyl-methyl)-5-nitro-imidazole;
131. 1-methyl-2-(2-methoxy-pyrimidinyl-4-sulfinyl-methyl)-5-nitro-imidazole;
132. 1-methyl-2-(6-methoxy-pyrimidinyl-4-sulfinyl-methyl)-5-nitro-imidazole;
133. 1-methyl-2-(2,6-dimethyl-pyrimidinyl-4-sulfinyl-methyl)-5-nitro-imidazole;
134. 1-methyl-2-(2,6-dimethoxy-pyrimidinyl-4-sulfinyl-methyl)-5-nitro-imidazole;
135. 1-methyl-2-(2-methyl-6-methoxy-pyrimidinyl-4-sulfinyl-methyl)-5-nitro-imidazole;
136. 1-methyl-2-(2-methoxy-6-methyl-pyrimidinyl-4-sulfinyl-methyl)-5-nitro-imidazole;
137. 1-methyl-2-(3-methyl-pyrazinyl-2-sulfinyl-methyl)-5-nitro-imidazole;
138. 1-methyl-2-(5-methyl-pyrazinyl-2-sulfinyl-methyl)-5-nitro-imidazole;
139. 1-methyl-2-(3-methoxy-pyrazinyl-2-sulfinyl-methyl)-5-nitro-imidazole;
140. 1-methyl-2-(5-methoxy-pyrazinyl-2-sulfinyl-methyl)-5-nitro-imidazole;
141. 1-ethyl-2-(pyridazinyl-3-sulfinyl-methyl)-5-nitro-imidazole;
142. 1-ethyl-2-(pyrimidinyl-2-sulfinyl-methyl)-5-nitro-imidazole;
143. 1-ethyl-2-(5-fluoro-pyrimidinyl-2-sulfinyl-methyl)-5-nitro-imidazole;
144. 1-ethyl-2-(5-chloro-pyrimidinyl-2-sulfinyl-methyl)-5-nitro-imidazole;
145. 1-ethyl-2-(5-bromo-pyrimidinyl-2-sulfinyl-methyl)-5-nitro-imidazole;
146. 1-ethyl-2-(pyrimidinyl-4-sulfinyl-methyl)-5-nitro-imidazole;
147. 1-ethyl-2-(5-fluoro-pyrimidinyl-4-sulfinyl-methyl)-5-nitro-imidazole;
148. 1-ethyl-2-(5-chloro-pyrimidinyl-4-sulfinyl-methyl)-5-nitro-imidazole;
149. 1-ethyl-2-(5-bromo-pyrimidinyl-4-sulfinyl-methyl)-5-nitro-imidazole;
150. 1-ethyl-2-(pyrazinyl-2-sulfinylmethyl)-5-nitro-imidazole;
151. 1-methyl-2-[pyridazinyl-3-sulfinyl-(1-ethyl)]-5-nitro-imidazole;
152. 1-methyl-2-[pyrimidinyl-2-sulfinyl-(1-ethyl)]-5-nitro-imidazole;
153. 1-methyl-2-[5-fluoro-pyrimidinyl-2-sulfinyl-(1-ethyl)]-5-nitro-imidazole;
154. 1-methyl-2-[5-chloro-pyrimidinyl-2-sulfinyl-(1-ethyl)]-5-nitro-imidazole;
155. 1-methyl-2-[5-bromo-pyrimidinyl-2-sulfinyl-(1-ethyl)]-5-nitro-imidazole;
156. 1-methyl-2-[pyrimidinyl-4-sulfinyl-(1-ethyl)]-5-nitro-imidazole;
157. 1-methyl-2-[5-fluoro-pyrimidinyl-4-sulfinyl-(1-ethyl)]-5-nitro-imidazole;
158. 1-methyl-2-[5-chloro-pyrimidinyl-4-sulfinyl-(1-ethyl)]-5-nitro-imidazole;
159. 1-methyl-2-[5-bromo-pyrimidinyl-4-sulfinyl-(1-ethyl)-]-5-nitro-imidazole;
160. 1-methyl-2-[pyrazinyl-2-sulfinyl-(1-ethyl)]-5-nitro-imidazole.
161. 1-Methyl-2-(pyrimidinyl-2-sulfonyl-methyl)-5-nitro-imidazole 25.1 Grams (0.1 mol) of 1-methyl-2-(pyrimidinyl-2-sulfonyl-methyl)-5 nitro-imidazole were dissolved in 400 ml of glacial acetic acid, and 20.0 ml (0.2 mol) of 35% hydrogen peroxide were added dropwise, while stirring, at room temperature. Stirring was then continued for 2 hours, while heating on a steam bath. The reaction solution was concentrated by evaporation under reduced pressure, and the residue was recrystallized from water/alcohol.

Thus, 20.7 g of 1-methyl-2-(pyrimidinyl-2-sulfonyl-methyl)-5-nitro-imidazole (corresponding to 73% of the theoretical yield) were obtained in the form of yellowish crystals, melting point 184° C.

In the same manner, the following compounds were obtained in good yields by oxidation of the corresponding thio compounds:

162. 1-methyl-2-(pyridazinyl-3-sulfonyl-methyl)-5-nitro-imidazole;
163. 1-methyl-2-(5-fluoro-pyrimidinyl-2-sulfonyl-methyl)-5-nitro-imidazole;
164. 1-methyl-2-(5-chloro-pyrimidinyl-2-sulfonyl-methyl)-5-nitro-imidazole;
165. 1-methyl-2-(5-bromo-pyrimidinyl-2-sulfonyl-methyl)-5-nitro-imidazole;
166. 1-methyl-2-(pyrimidinyl-4-sulfonyl-methyl)-5-nitro-imidazole;
167. 1-methyl-2-(5-fluoro-pyrimidinyl-4-sulfonyl-methyl)-5-nitro-imidazole;
168. 1-methyl-2-(5-chloro-pyrimidinyl-4-sulfonyl-methyl)-5-nitro-imidazole;
169. 1-methyl-2-(5-bromo-pyrimidinyl-4-sulfonyl-methyl)-5-nitro-imidazole;
170. 1-methyl-2-(pyrazinyl-2-sulfonyl-methyl)-5-nitro-imidazole;

171. 1-methyl-2-(6-methyl-pyridazinyl-3-sulfonyl-methyl)-5-nitro-imidazole;
172. 1-methyl-2-(6-methoxy-pyridazinyl-3-sulfonyl-methyl)-5-nitro-imidazole;
173. 1-methyl-2-(4-methyl-pyrimidinyl-2-sulfonyl-methyl)-5-nitro-imidazole;
174. 1-methyl-2-(5-methyl-pyrimidinyl-2-sulfonyl-methyl)-5-nitro-imidazole;
175. 1-methyl-2-(4-methoxy-pyrimidinyl-2-sulfonyl-methyl)-5-nitro-imidazole;
176. 1-methyl-2-(5-methoxy-pyrimidinyl-2-sulfonyl-methyl)-5-nitro-imidazole;
177. 1-methyl-2-(4,6-dimethyl-pyrimidinyl-2-sulfonyl-methyl)-5-nitro-imidazole;
178. 1-methyl-2-(4,6-dimethoxy-pyrimidinyl-2-sulfonyl-methyl)-5-nitro-imidazole;
179. 1-methyl-2-(4-methyl-6-methoxy-pyrimidinyl-2-sulfonyl-methyl)-5-nitro-imidazole;
180. 1-methyl-2-(2-methyl-pyrimidinyl-4-sulfonyl-methyl)-5-nitro-imidazole;
181. 1-methyl-2-(6-methyl-pyrimidinyl-4-sulfonyl-methyl)-5-nitro-imidazole;
182. 1-methyl-2(2-methoxy-pyrimidinyl-4-sulfonyl-methyl)-5-nitro-imidazole;
183. 1-methyl-2-(6-methoxy-pyrimidinyl-4-sulfonyl-methyl)-5-nitro-imidazole;
184. 1-methyl-2-(2,6-dimethyl-pyrimidinyl-4-sulfonyl-methyl)-5-nitro-imidazole;
185. 1-methyl-2-(2,6-dimethoxy-pyrimidinyl-4-sulfonyl-methyl)-5-nitro-imidazole;
186. 1-methyl-2-(2-methyl-6-methoxy-pyrimidinyl-4-sulfonyl-methyl)-5-nitro-imidazole;
187. 1-methyl-2-(2-methoxy-6-methyl-pyrimidinyl-4-sulfonyl-methyl)-5-nitro-imidazole;
188. 1-methyl-2-(3-methyl-pyrazinyl-2-sulfonyl-methyl)-5-nitro-imidazole;
189. 1-methyl-2-(5-methyl-pyrazinyl-2-sulfonyl-methyl)-5-nitro-imidazole;
190. 1-methyl-2-(3-methoxy-pyrazinyl-2-sulfonyl-methyl)-5-nitro-imidazole;
191. 1-methyl-2-(5-methoxy-pyrazinyl-2-sulfonyl-methyl)-5-nitro-imidazole;
192. 1-ethyl-2-(pyridazinyl-3-sulfonyl-methyl)-5-nitro-imidazole;
193. 1-ethyl-2-(pyrimidinyl-2-sulfonyl-methyl)-5-nitro-imidazole;
194. 1-ethyl-2-(5-fluoro-pyrimidinyl-2-sulfonyl-methyl)-5-nitro-imidazole;
195. 1-ethyl-2-(5-chloro-pyrimidinyl-2-sulfonyl-methyl)-5-nitro-imidazole;
196. 1-ethyl-2-(5-bromo-pyrimidinyl-2-sulfonyl-methyl)-5-nitro-imidazole;
197. 1-ethyl-2-(pyrimidinyl-4-sulfonyl-methyl)-5-nitro-imidazole;
198. 1-ethyl-2-(5-fluoro-pyrimidinyl-4-sulfonyl-methyl)-5-nitro-imidazole;
199. 1-ethyl-2-(5-chloro-pyrimidinyl-4-sulfonyl-methyl)-5-nitro-imidazole;
200. 1-ethyl-2-(5-bromo-pyrimidinyl-4-sulfonyl-methyl)-5-nitro-imidazole;
201. 1-ethyl-2-(pyrazinyl-2-sulfonyl-methyl)-5-nitro-imidazole;
202. 1-methyl-2-[pyridazinyl-3-sulfonyl-(1-ethyl)]-5-nitro-imidazole;
203. 1methyl-2-[pyrimidinyl-2-sulfonyl-(1-ethyl)]-5-nitro-imidazole;
204. 1-methyl-2-[5-fluoro-pyrimidinyl-2-sulfonyl-(1ethyl)]-5-nitro-imidazole;
205. 1-methyl-2-[5-chloro-pyrimidinyl-2-sulfonyl-(1-ethyl)]-5-nitro-imidazole;
206. 1-methyl-2-[5-bromo-pyrimidinyl-2-sulfonyl-(1-ethyl)]-5-nitro-imidazole;
207. 1-methyl-2-[pyrimidinyl-4-sulfonyl-(1-ethyl)]-5-nitro-imidazole;
208. 1-methyl-2-[5-fluoro-pyrimidinyl-4-sulfonyl-(1-ethyl)]-5-nitro-imidazole;
209. 1methyl-2-[5-chloro-pyrimidinyl-4-sulfonyl-(1-ethyl)]-5-nitro-imidazole;
210. 1methyl-2-[5-bromo-pyrimidinyl-4-sulfonyl-(1-ethyl)]-5-nitro-imidazole;
211. 1-methyl-2-[pyrazinyl-2-sulfonyl-(1-ethyl)]-5-nitro-imidazole.

212. By reacting 25.2 g (0.1 mol) of 1-methyl-2-(S-isothiouronium-methyl)-5-nitro-imidazole hydrochloride and 11.5 g (0.1 mol) of 2-chloropyrimidine in 250 ml of dimethyl formamide, in the presence of 10.8 g (0.2 mol) of sodium methylate, during 1 hour at a temperature of from 35° to 45° C, and after cooling and adding water until crystallization started, 1-methyl-2-(pyrimidinyl-2-thiomethyl)-5-nitro-imidazole was obtained, which had a melting point of 143° C.

The 1-methyl-2-(S-isothiouronium-methyl)-5-nitro-imidazole hydrochloride used as starting product has been known from Deutsche Offenlegungsschrift No. 2,124,103 and was prepared by reacting 1-methyl-2-chloromethyl-5-nitro-imidazole with thiourea.

The compounds prepared according to Examples 2 to 211 may also be obtained in an analogous manner.

We claim:
1. A (1-alkyl-5-nitro-imidazolyl-2-alkyl)-heteroaryl compound of the formula

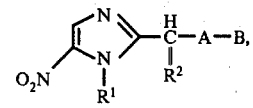

wherein $R^1$ is methyl or ethyl, $R^2$ is hydrogen or methyl, A is sulfur, sulfoxide or sulfone, B is

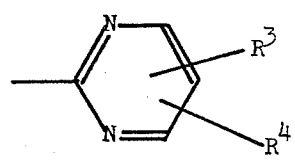 or 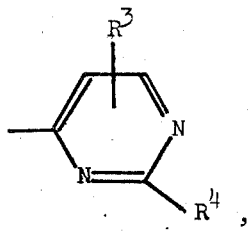

and $R^3$ and $R^4$, which may be the same or different, are hydrogen, methyl, methoxy, halogen, cyano, or nitro.

2. A compound as claimed in claim 1, which is 1-methyl-2-(pyrimidinyl-2-thiomethyl)-5-nitro-imidazole.

3. A compound as claimed in claim 1, which is 1-methyl-2-(4-methoxy-pyrimidinyl-2-thiomethyl)-5-nitro-imidazole.

4. A compound as claimed in claim 1, which is 1-methyl-2-(4-methyl)-6-methoxy-pyrimidinyl-2-thiomethyl)-5-nitro-imidazole.

5. A compound as claimed in claim 1, which is 1-methyl-2-(pyrimidinyl-4-thiomethyl)-5-nitro-imidazole.

6. A compound as claimed in claim 1, which is 1-methyl-2-(2,6-dimethyl-pyrimidinyl-4-thiomethyl)-5-nitro-imidazole.

7. A pharmaceutical composition for the treatment of protozoal diseases, said composition comprising an amount of a compound as in claim 1 which is effective against protozoa in combination with a pharmaceutical excipient.

8. A pharmaceutical composition as in claim 7 in the form of a jelly, cream, ointment, or suppository for local administration.

9. A pharmaceutical composition as in claim 7 in dosage unit form for oral administration and containing from 10 mg to 750 mg of said compound.

10. A method for combatting a protozoal infection in a mammal suffering therefrom which comprises orally or locally administering an amount of a compound as in claim 1 in an amount effective against said protozoal infection.

* * * * *